US010765528B2

(12) United States Patent
Weiman et al.

(10) Patent No.: US 10,765,528 B2
(45) Date of Patent: Sep. 8, 2020

(54) ARTICULATING EXPANDABLE INTERVERTEBRAL IMPLANT

(71) Applicant: GLOBUS MEDICAL, INC., Audubon, PA (US)

(72) Inventors: Mark Weiman, Coatesville, PA (US); John Matthews, Philadelphia, PA (US)

(73) Assignee: Globus Medical Inc., Audubon, PA (US)

( * ) Notice: Subject to any disclaimer, the term of this patent is extended or adjusted under 35 U.S.C. 154(b) by 140 days.

(21) Appl. No.: 14/929,569

(22) Filed: Nov. 2, 2015

(65) Prior Publication Data

US 2016/0051377 A1 Feb. 25, 2016

Related U.S. Application Data

(63) Continuation of application No. 13/782,724, filed on Mar. 1, 2013, now Pat. No. 9,204,972.

(51) Int. Cl.
*A61F 2/44* (2006.01)
*A61F 2/30* (2006.01)
*A61F 2/46* (2006.01)

(52) U.S. Cl.
CPC ............ *A61F 2/4465* (2013.01); *A61F 2/442* (2013.01); *A61F 2/447* (2013.01); *A61F 2/4425* (2013.01); *A61F 2/4455* (2013.01); *A61F 2002/30387* (2013.01); *A61F 2002/30507* (2013.01); *A61F 2002/30538* (2013.01); *A61F 2002/30556* (2013.01); *A61F 2002/30579* (2013.01); *A61F 2002/30772* (2013.01); *A61F 2002/30904* (2013.01); *A61F 2002/443* (2013.01); *A61F 2002/4629* (2013.01)

(58) Field of Classification Search
CPC .......... A61F 2/44; A61F 2/442; A61F 2/4425; A61F 2/4455–447; A61F 2002/443
See application file for complete search history.

(56) References Cited

U.S. PATENT DOCUMENTS

| 5,865,848 | A | 2/1999 | Baker |
| 7,070,598 | B2 | 7/2006 | Lim et al. |
| 7,909,876 | B2 | 3/2011 | Dooris et al. |
| 8,211,178 | B2 | 7/2012 | Melkent et al. |
| 8,900,305 | B2 | 12/2014 | Stad et al. |

(Continued)

FOREIGN PATENT DOCUMENTS

| JP | 2006516456 A | 7/2006 |
| JP | 2008126085 A | 6/2008 |

*Primary Examiner* — Amy R Sipp

(57) ABSTRACT

A spacer for separating bones of a joint includes a frame and a carriage. The carriage has ramped surfaces, and is slideably moveable in relation to the frame. A screw support is moveably connected to the frame to form a changeable angular orientation with respect to the frame. An actuating screw is supported by the screw support, and is connected to the carriage to cause the carriage to slideably move in relation to the frame when the actuating screw is rotated. Opposing endplates are configured to engage opposing bone of the joint, and each has ramped surfaces mateable with the ramped surfaces of the carriage. When the carriage is moved by rotation of the actuating screw, the ramped surfaces of the carriage and the endplates slide against each other, causing the endplates to move relatively apart, to increase the height of the spacer.

18 Claims, 5 Drawing Sheets

(56) References Cited

U.S. PATENT DOCUMENTS

| | | |
|---|---|---|
| 2004/0087947 A1 | 5/2004 | Lim et al. |
| 2004/0153065 A1 | 8/2004 | Lim |
| 2005/0209698 A1 | 9/2005 | Gordon et al. |
| 2008/0147193 A1* | 6/2008 | Matthis ................. A61F 2/4425 623/17.16 |
| 2011/0093074 A1* | 4/2011 | Glerum ................... A61F 2/447 623/17.16 |
| 2011/0172774 A1* | 7/2011 | Varela ................... A61F 2/4611 623/17.16 |
| 2012/0323328 A1* | 12/2012 | Weiman ................... A61F 2/447 623/17.16 |
| 2012/0330421 A1* | 12/2012 | Weiman ................... A61F 2/442 623/17.16 |
| 2013/0023994 A1* | 1/2013 | Glerum ................... A61F 2/447 623/17.16 |
| 2013/0158663 A1 | 6/2013 | Miller et al. |
| 2014/0249628 A1 | 9/2014 | Weiman |

* cited by examiner

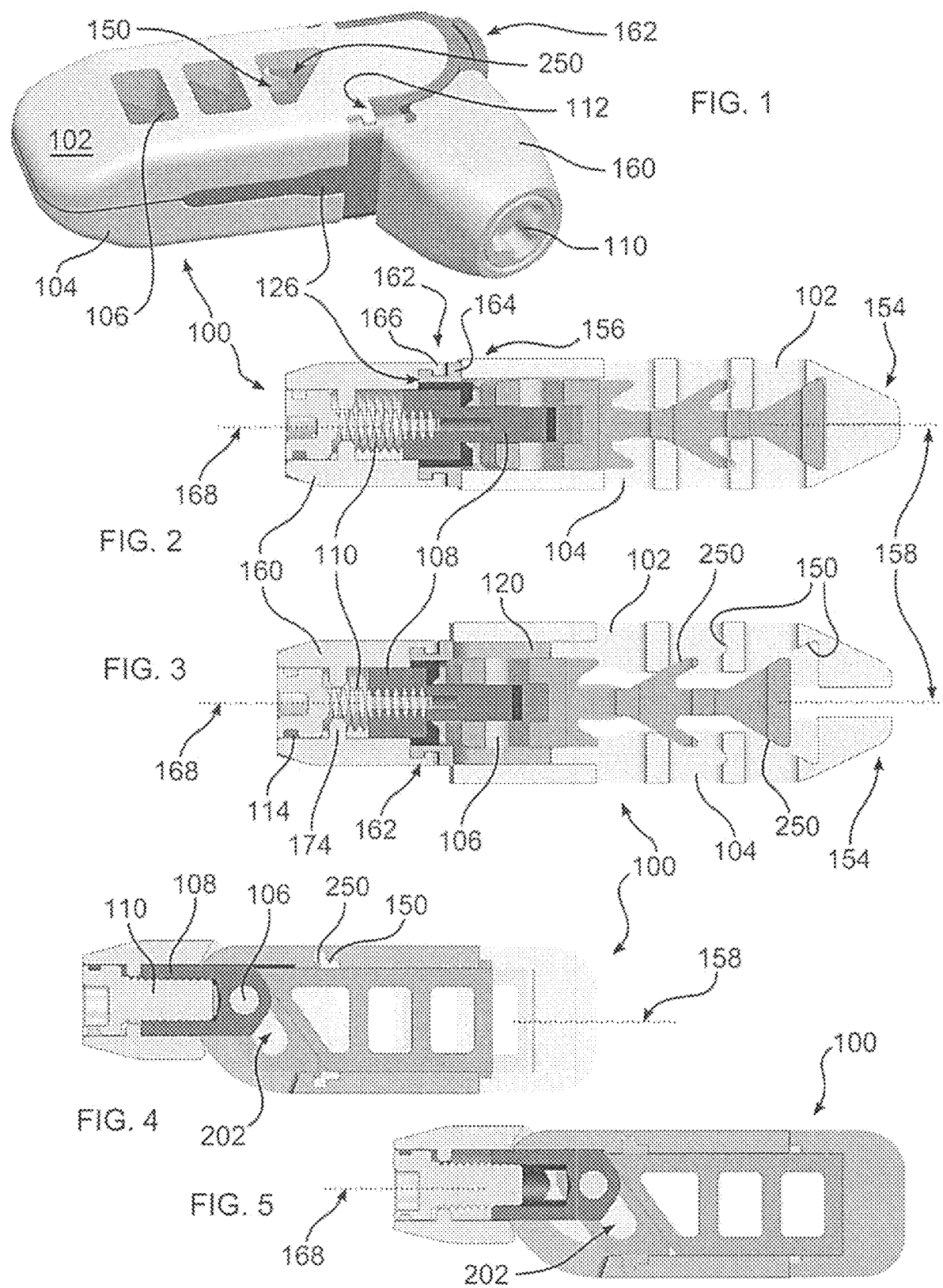

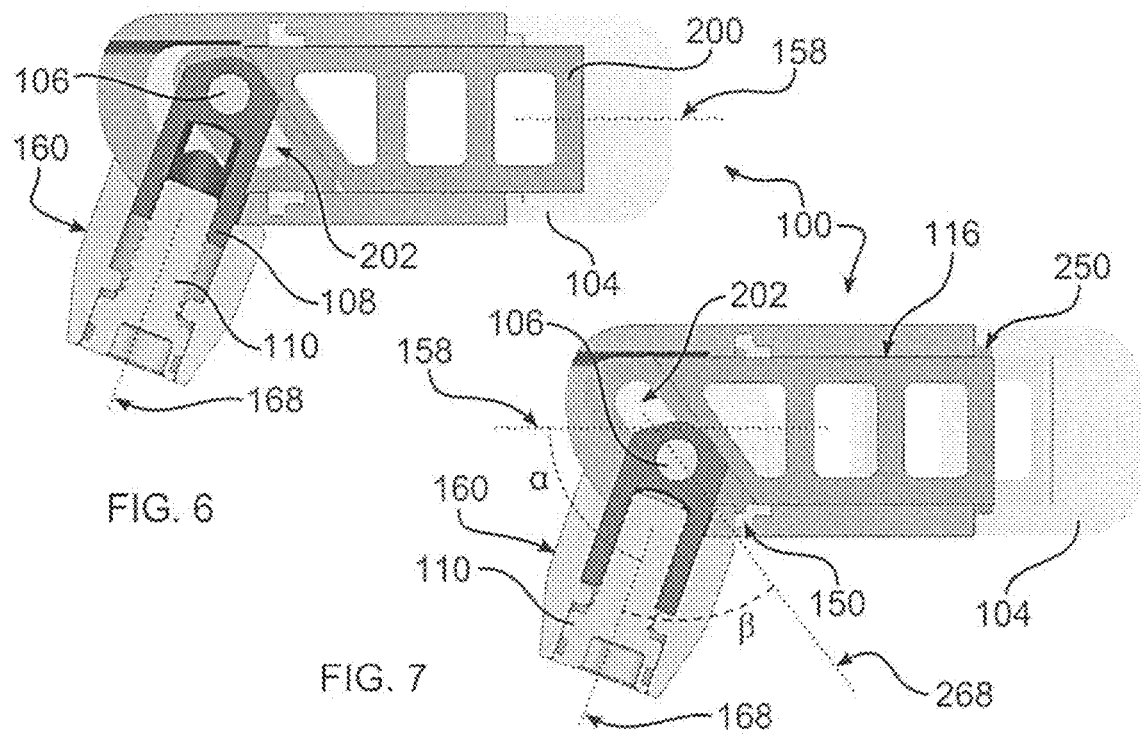
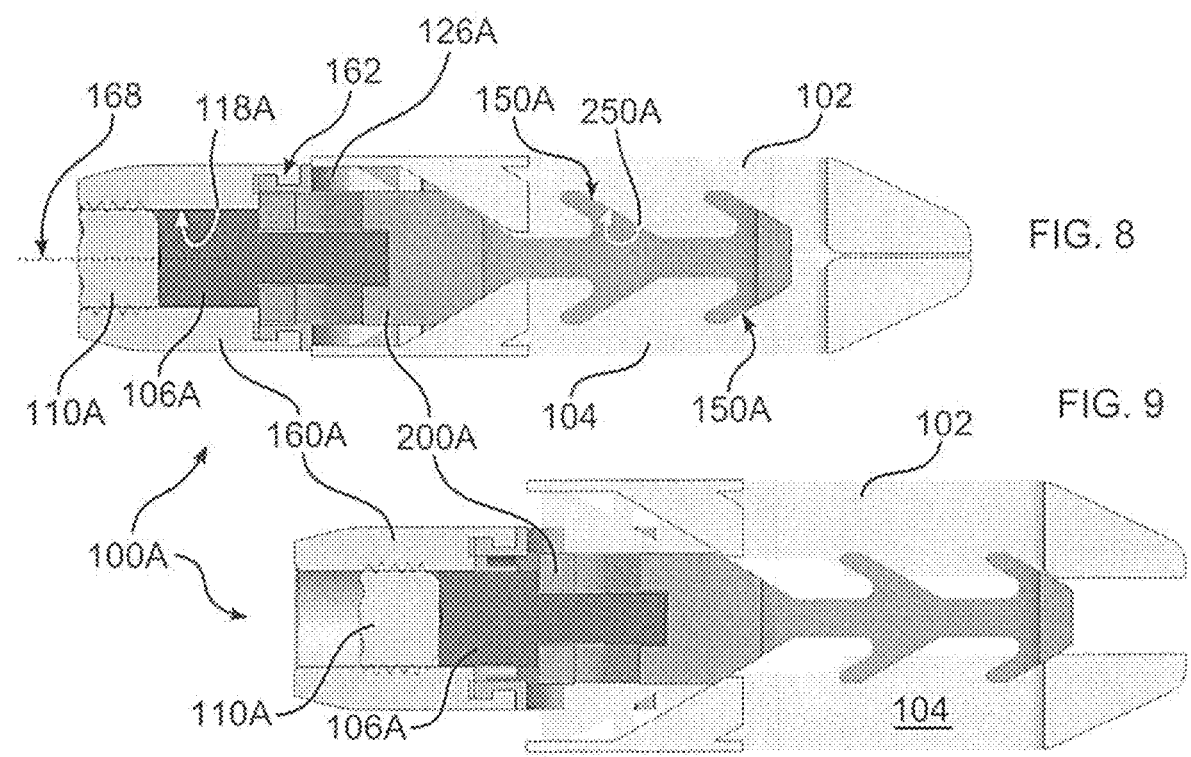

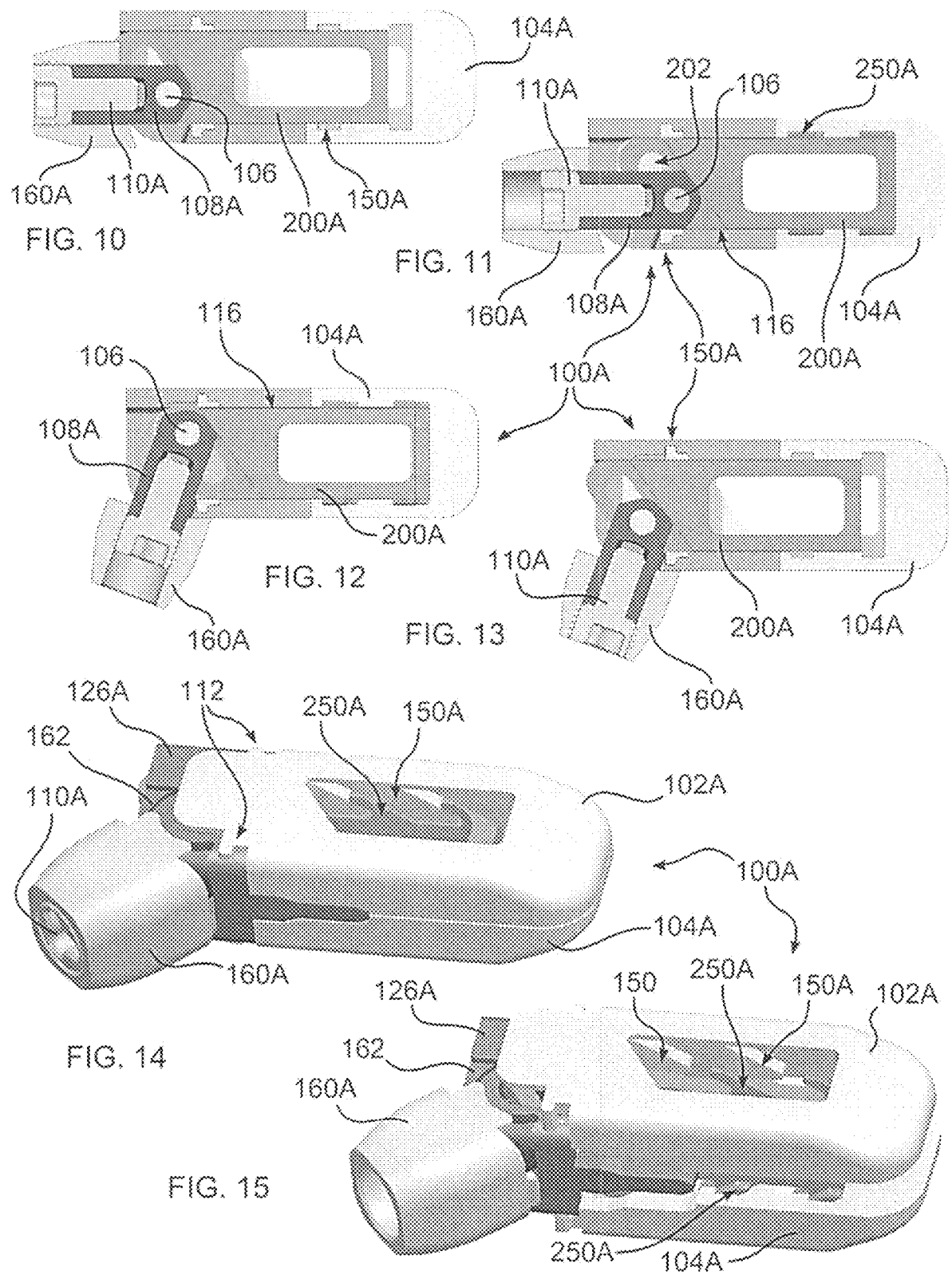

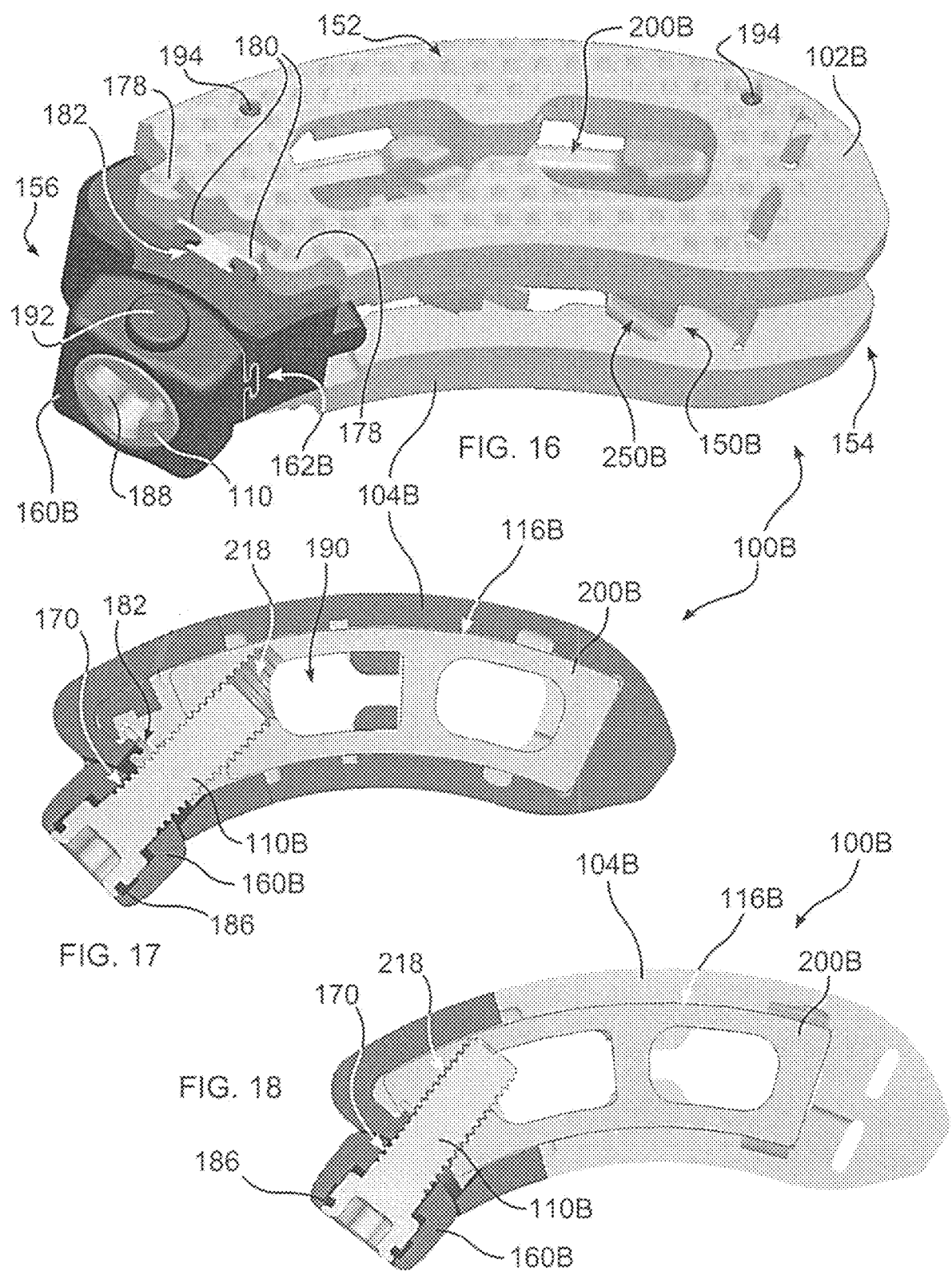

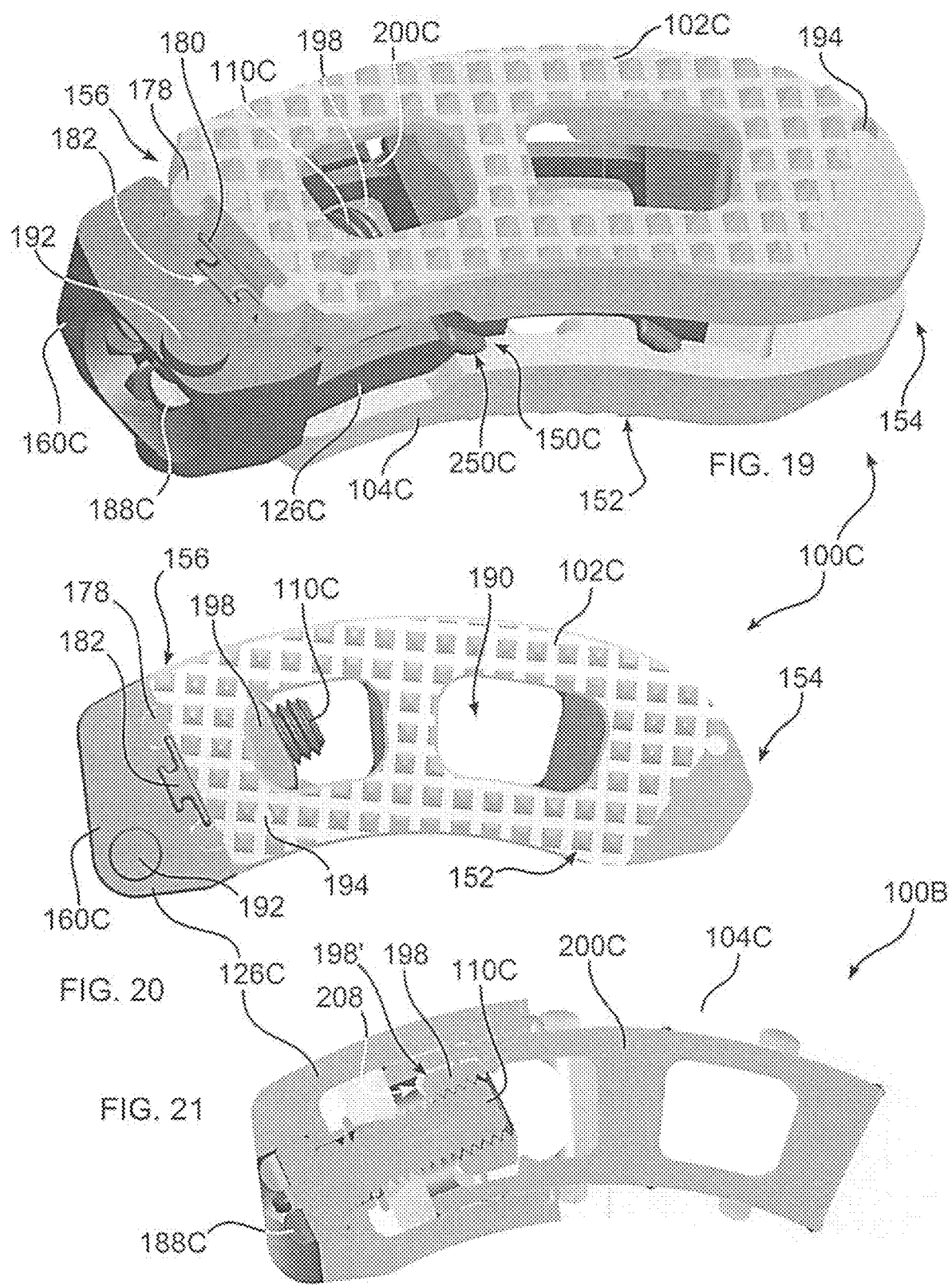

ARTICULATING EXPANDABLE INTERVERTEBRAL IMPLANT

CROSS REFERENCE TO RELATED APPLICATIONS

The present application is a continuation of U.S. patent application Ser. No. 13/782,724, filed on Mar. 1, 2013, which is incorporated by reference in its entirety herein.

FIELD OF THE INVENTION

This invention relates to stabilizing adjacent vertebrae of the spine by inserting an intervertebral spacer, and more particularly an intervertebral spacer that is adjustable in height, and a tool therefore.

BACKGROUND OF THE INVENTION

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intevertebral disc, such as normal physiological aging, mechanical injury/trauma, and/or disease, resulting in impairment or loss of disc function. For example, the content of proteoglycan in the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY OF THE INVENTION

In accordance with an embodiment of the disclosure, a spacer for separating bones of a joint comprises a frame; a carriage slideably moveable in relation to the frame, and having at least one ramped surface; an actuating screw connected to the carriage and supported by the frame, the actuating screw configured to cause the carriage to slideably move in relation to the frame when the actuating screw is rotated; a first endplate configured to engage a first bone of the joint, and having at least one ramped surface mateable with the at least one carriage ramped surface, whereby when the carriage is slideably moved by rotation of the actuating screw, the at least one endplate ramped surface slides against the at least one carriage ramped surface to cause the first endplate to move along an axis transverse to the longitudinal axis, to increase a height of the spacer; and a second endplate configured to engage a second bone of the joint.

In various embodiments thereof, the carriage includes a threaded bore into which the actuating screw is threaded; the endplate is continuously curved along its length; the actuating screw is secured to the carriage by a nut; the nut and the carriage form a mating, curved bearing surface therebetween; the spacer further includes a screw support connected to the frame and configured to rotatably retain the actuating screw; the screw support forms a longitudinal axis, and the frame forms a longitudinal axis, the screw support being slideably connected to the frame to enable changing an angular orientation between the actuating screw and the frame.

In other embodiments thereof, the screw is rotatable at a plurality of angular orientations of the actuating screw and the frame; the screw support is slideably connected to the frame by a flanged connection; the first endplate is connected to the frame by a slideable flanged connection.

In another embodiment thereof, the spacer further includes a pin moveable within a slot formed in the carriage; and a link pivotably mounted to the pin, and including a threaded bore into which the actuating screw is threadably engageable to cause the carriage to slideably move within the frame.

In yet further embodiments thereof, the first endplate is slideably retained in connection with the frame by a flanged connection; the spacer further includes a screw support pivotally connected to the frame and rotatably supporting the actuating screw; the carriage includes at least two ramped surfaces, and the second endplate includes at least one ramped surface mateable with at least one of the at least two ramped surfaces of the carriage, whereby when the carriage is slideably moved by rotation of the actuating screw, the at least one second endplate ramped surface slides against the at least one additional carriage ramped surface to cause the second endplate to move along an axis transverse to the longitudinal axis to increase a height of the spacer.

In other embodiments thereof, the first endplate is configured to abut the frame as the first endplate is moved along an axis transverse to the longitudinal axis, whereby the first endplate moves substantially only along an axis transverse to the longitudinal axis; at least one of the first endplate and the frame includes at least one aperture through which a fastener may pass to secure the spacer to a bone of the joint; the spacer further includes a blocking mechanism to prevent backing out of a fastener passed through the first endplate; the first endplate includes one or more projections configured to engage bone of the joint when the implant is positioned between bones of the joint.

In another embodiment of the disclosure, a method of separating bones of a joint comprises inserting a spacer between bones of the joint, the spacer including a frame; a carriage slideably moveable in relation to the frame, and having at least one ramped surface; an actuating screw connected to the carriage and supported by the frame, the actuating screw configured to cause the carriage to slideably move in relation to the frame when the actuating screw is rotated; a first endplate configured to engage a first bone of the joint, and having at least one surface mateable with the at least one carriage ramped surface, whereby when the carriage is slideably moveable by rotation of the actuating screw, the at least one endplate ramped surface slides against the at least one carriage ramped surface to cause the first endplate to move along an axis transverse to the longitudinal axis, to increase a height of the spacer; and a second endplate configured to engage a second bone of the joint.

In a yet further embodiment of the disclosure, a spacer for separating bones of a joint comprises a frame; a carriage slideably moveable in relation to the frame, and having at least two ramped surfaces; a screw support moveably connected to the frame to form a changeable angular orientation with respect to the frame; an actuating screw supported by the screw support and connected to the carriage, the actuating screw configured to cause the carriage to slideably move in relation to the frame when the actuating screw is rotated; and first and second endplates each configured to engage an opposing bone of the joint, each having at least one ramped surface mateable with at least one of the at least two carriage ramped surfaces, whereby when the carriage is slideably moved by rotation of the actuating screw, the at least one ramped surface of each of the first and second endplates slides against the at least one carriage ramped surface to cause the first and second endplates to move relatively apart along an axis transverse to the longitudinal axis, to increase a height of the spacer.

BRIEF DESCRIPTION OF THE DRAWINGS

A more complete understanding of the disclosure, and the attendant advantages and features thereof, will be more readily understood by reference to the following detailed description when considered in conjunction with the accompanying drawings, in which:

FIG. 1 is a perspective view of a spacer implant of the disclosure, with an articulating screw support;

FIG. 2 depicts a cross section of the spacer of FIG. 1, taken through an actuating screw of the spacer, with the screw support oriented longitudinally, as further illustrated in FIGS. 4 and 5;

FIG. 3 depicts the cross section of FIG. 2, with the spacer expanded by a separation of endplates;

FIG. 4 depicts the spacer of FIG. 3, taken along an orientation 90 degrees offset from the orientation of the spacer of FIG. 3;

FIG. 5 depicts the spacer of FIG. 2, taken along an orientation 90 degrees offset from the orientation of the spacer of FIG. 2;

FIG. 6 depicts a cross section through the spacer of FIG. 1;

FIG. 7 depicts the spacer of FIG. 6, the endplates relatively separated;

FIG. 8 depicts a cross section of an alternative spacer of the disclosure shown in FIG. 14, the endplates separated by pushing a carriage, having a screw support aligned with a longitudinal axis of the spacer;

FIG. 9 depicts the spacer of FIG. 8, the endplates separated;

FIG. 10 depicts the spacer of FIG. 8, taken along an orientation 90 degrees offset from the orientation of the spacer of FIG. 8;

FIG. 11 depicts the spacer of FIG. 10, the endplates separated;

FIG. 12 depicts the spacer of FIG. 11, the screw support disposed at an angle with respect to the frame;

FIG. 13 depicts the spacer of FIG. 10, the screw support disposed at an angle with respect to the frame;

FIG. 14 is a perspective view of an alternative embodiment of a spacer of the disclosure, including a carriage which is pushed to separate endplates, and an actuator screw which is displaced within a screw support;

FIG. 15 depicts the spacer of FIG. 14, the endplates separated;

FIG. 16 is a perspective view of an alternative spacer embodiment of the disclosure, having a curved shape;

FIG. 17 depicts a cross section of the spacer of FIG. 16, the endplates not separated;

FIG. 18 depicts a cross section of the spacer of FIG. 16;

FIG. 19 is a perspective view of an alternative spacer embodiment of the disclosure, the actuating screw secured to the carriage by a nut;

FIG. 20 depicts a top view of the spacer of FIG. 19; and

FIG. 21 is a cross section of the spacer of FIG. 19.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

With reference to FIGS. 1-3, the disclosure provides an expandable spacer 100 having an adjustable height. The implant is inserted between two adjacent bony surfaces to facilitate separation of the bones, and if desired, can promote the fusion of the bony surfaces. Although intended to be useful with any adjacent bony surface in which fusion is desired, the implant is advantageously applied to insertion between two adjacent vertebral bodies in any section of the spine, including the cervical, thoracic, lumbar, and sacral vertebral sections. More than one spacer 100 may be implanted within the body, for example between successive or separated vertebrae, between adjacent vertebrae. The use of multiple implants is particularly advantageous for patients whose back pain is not limited to a localized area, or for patients whose localized damage has progressed to other areas of the spine.

The implant and methods for its insertion can be used in a treatment protocol for any of a wide variety of conditions in a patient involving diseased or damaged bony structures. The patient can be a human being. Additionally, it is contemplated that the implant may be useful in veterinary science for any animal having adjacent bony structures to be fused. The implant can collapse, for example, to approximately one half of an expanded size. When in this collapsed configuration, the implant can be inserted into a space through a small incision and narrow pathways, using appropriate minimally-invasive techniques, and can be positioned within the space between adjacent bones, and there expanded to a desired therapeutic height. The incision may be short, for example about one inch in length, which is smaller than the implant in an expanded configuration. If the desired position and/or expansion are not achieved, the implant can be collapsed, repositioned, and re-expanded in situ.

Although the implant is exemplified herein for use in the spine, the implant is contemplated for fusion of any bony structures. While the implants are described herein using several varying embodiments, the implants are not limited to these embodiments. An element of one embodiment may be used in another embodiment, or an embodiment may not include all described elements.

With reference to FIGS. 1-5, a spacer 100 of the disclosure includes endplates 102, 104 having expansion ramps 150, mateable with moveable lift ramps 250 of a carriage 200. In the embodiment shown, endplates 102, 104 are symmetrical, and spacer 100 can be implanted with either endplate positioned superior with respect to the other. In other embodiments, they may be dissimilar, and a particular orientation may then be advantageous or necessary.

Spacer 100 forms a distal end 154 which is inserted first into the body, and which can be tapered to facilitate insertion between body tissue, and a proximal end 156, to which a tool may be connected. Distal and proximal ends 154 and 156 define a longitudinal plane 158, extending therebetween. To expand Spacer 100, lift ramps 250 are displaced relative to endplates 102, 104, causing expansion ramps 150 to slide along lift ramps 250, thereby moving endplates 102, 104 relatively apart, thereby increasing a height of Spacer 100. Body tissue engaging projections 152, for example tooth shaped projections, can be provided upon a surface of endplate 102, 104, to further secure spacer 100 in a therapeutic location.

Lift ramps 250 extend from carriage 200, which is slideably retained within a frame 126 extending between endplates 102, 104. Carriage 200 is displaced relative to endplates 102, 104 by being pulled by a pin 106 connected to a link 108 threadably connected to an actuating screw 110. One or more guide elements 112, associated with frame 126, can be provided to prevent endplates 102, 104 from moving along longitudinal axis 158 along with carriage 200, thereby causing lift ramps 250 and expansion ramps 150 to be moved relative to each other, expanding or contracting Spacer 100. Actuating screw can be prevented from moving along longitudinal axis by a blocking flange 114 or 174.

With further reference to FIGS. 6-7, in accordance with the disclosure, an articulating screw support 160 is slideably retained in connection with frame 126 by, in one embodiment, a flanged connection 162. In this manner, a longitudinal axis 168, defined by screw support 160 and pin 106, may form a changeable angle (α) with respect to longitudinal axis 158 of endplates 102, 104, or a longitudinal axis of frame 126. Actuating screw 110 is rotatably confined within screw support 160, and is threadably engaged with link 108. Pin 106 pivotally retains link 108 in connection with carriage 200. A slot 202, associated with carriage 200, enables movement of pin 106, whereby pin 106 and link 108 can maintain a fixed orientation with respect to screw support 160, regardless of an angular disposition of screw support 160. Slot 202 is thus configured and dimensioned to enable a location of pin 106, confined therewithin, to correspond to a path of travel of screw support 160 as defined by connection 162.

In one embodiment, a path of travel of screw support 160 is defined by connection 162 to maintain a fixed orientation of carriage 200 with respect to frame 126. More particularly, if screw support 160 is moved along a path which does not pivot about a single point defined by a current location of pin 106, pin 106 may move within slot 202 to maintain a fixed distance in a contracted position between pin 106 and screw support 160, and therefore carriage 200 is not caused to be moved as screw support 160 is moved. In other embodiments, slot 202 is defined to cause a predetermined movement of carriage 200 as screw support 160 is moved.

Similarly, regardless of a given orientation of screw support 160, rotation of actuating screw advances or retards link 108 and pin 106, causing movement of carriage 200 relative to endplates 102, 104. More particularly, slot 202 defines a longitudinal axis 268, which is oriented to lie at a non-perpendicular angle ($\beta$) with respect to longitudinal axis 168 of screw support 160, through a substantial portion of the range of motion of screw support 160. In this manner, once a desired orientation of screw support 160 has been established, rotation of actuating screw 110 causes pin 106 to push or pull along an edge of slot 202, thereby causing movement of carriage 200. If axis 168 and 268 are perfectly perpendicular, it is possible no movement can be caused by threading screw 110; however, as a practical matter, reorienting screw support 160 a very small amount can resolve this theoretical limitation. Carriage 200 is slideably retained by a channel or edge interface 116 formed between carriage 200 and at least one endplate 102, 104, thereby limiting movement of carriage 200 along longitudinal axis 158.

With reference to FIGS. 8-15, an alternative spacer 100A of the disclosure functions in analogous manner to the embodiment of FIGS. 1-7, however in this embodiment, rotation of actuating screw 110A causes carriage 200A to push endplates 102A, 104A to cause expansion. More particularly, an orientation of expansion ramps 150A and lift ramps 250A are oriented 180 degrees with respect to longitudinal axis 158. The embodiment of FIGS. 8-9 additionally illustrates an alternative actuating screw 110A configuration, in which screw 110A is rotatably connected to link 108A, and threadably connected within screw support 160A, whereby screw 110A moves along longitudinal axis 168 within a threaded bore 118A of screw support 160A. Screw 110A causes movement of link 108A, which advances or retards pin 106 within slot 202, to cause a corresponding movement of carriage 200A. As the various aspects of differing embodiments of the disclosure may be substituted where logical, generally, it may be seen that this alternative screw 110A configuration can be used with other embodiments of the disclosure, as well.

As may be seen in FIG. 2, for example, in one embodiment, connection 162 includes interlocking mating flanges 164, 166, associated with frame 126 and screw support 160, respectively. Flanges 164, 166 form mutually curved guide surfaces defining a path of movement for screw support 160 relative to frame 126, and retain screw support 160 in engagement with frame 126. Other configurations are possible, provided screw support 160 and frame 126 may form different angular dispositions with respect to each other, and wherein actuating screw 110 or 110A (FIG. 8) may interact with carriage 200 or 200A to slide carriage 200 or 200A with respect to frame 126, 126A.

Turning now to FIGS. 16-18, spacer 100B includes curved endplates 102B, 104B, and a curved carriage 200B slideable within edge interface 116B. Carriage 200B includes a threaded bore 218, into which actuating screw 110B is threaded. As screw 110B is rotated in a first direction, carriage 200B is moved towards distal end 154, and as screw 110B is rotated in a second, opposite direction, carriage 200B is moved away from distal end 154. Depending upon the angular direction of ramps 150B and 250B, endplates 102B, 104B are moved together or apart, as described with respect to the embodiments of FIGS. 1 and 8. Spacer 100B forms, overall, a curved shape, which can advantageously be rotated as it is inserted through a minimal incision, to thereby become implanted between adjacent bones. This reduces an extent of a requirement of rotating a spacer, within the body, prior to insertion between the bones, thus reducing an adverse impact to adjacent body tissue.

As actuating screw 110B threads into carriage 200B, shaft 140 and head 142 of screw 110B are angularly displaced with respect to screw support 160B. Accordingly, screw support 160B is provided with a gapped region 170, allowing movement of screw 110B. Additionally, screw support 160B is retained in connection with a frame 126B by a flanged connection 162B, in this case a dovetail connection. Connection 162B enables screw support 160B to be angled with respect to frame 126B, to facilitate access to screw 110B by a tool (not shown), when spacer 100B is implanted within the body, and to further enable screw 110B to change an angle with respect to frame 126B.

Frame 126B is connected to each of endplates 102B, 104B by a flanged connector, in this embodiment a dovetail formed between endplate flanges 178 extending from each of endplates 102B, 104B, and frame flanges 180 associated with an intermediate connector 182. Actuating screw 110B can be rotatably retained within screw support 160B by a washer or flange (not shown) positioned in groove 186 within screw support 160B, or intermediate connector 182 can be configured to rotatably retain screw 100B.

With reference to FIGS. 16-21, a spacer 100C functions in a similar manner to spacers 100, 100A, and 100B, with the following distinctions. Initially, in the embodiment shown, screw support 160C does not slide along a flanged connector 162, and is connected to endplates 102C, 104C in a like manner as spacer 100B. However, screw support 160C could be connected to a remainder of spacer 100C using a flange connector 162. Additionally, actuating screw 110C has a tool engagement 188C that is different than the tool engagement of other embodiments, although engagement style 188, or any other style tool engagement, may be provided upon screw 110C. Engagement stylet 188 allows for articulating between the holder and the implant by pivot point 192.

As may best be seen in FIG. 20, 21, nut 198 retains actuating screw 110C in connection with carriage 200C. However, in distinction with respect to threaded bore 218 of spacer 100B, nut 198 may toggle, or change an angular orientation with respect to carriage 200C, as screw 100C is rotated, and carriage 200C is moved. Nut 198 can be provided with a nut bearing surface 198', which mateably interacts with a carriage bearing surface 208. Similar bearing surfaces 198" and 208' can be provided on an opposite side of nut 198, for pushing carriage 200C in an opposite direction. In the embodiment shown, threading nut 198 in the direction of proximal end 156 causes an expansion or increase in height of spacer 100C, and threading nut 198 in a direction of distal end 154 causes a reduction, or decrease in height of spacer 100C. However, ramps 150C and 250C can be oriented to cause an opposite effect.

The following discussion pertains to all embodiments of the disclosure, including spacers 100, 100A, 100B, and 100C. For brevity, the letter suffix designating variations of like parts will be omitted, unless a specific distinction is made. For all spacer 100 embodiments of the disclosure, carriage 200 can be slid, or actuated, when screw support 60 is disposed at an angle with respect to the carriage. In the embodiments of FIGS. 1-15, this angle may vary between 0° and 70°, and with modifications, this angle could be increased to a theoretical maximum approaching 180°. The embodiment of FIGS. 16-18 accomplishes disposing screw 100B at an angle to the endplate bodies by curving the endplates, and by configuring bore 218 at an angle with respect to carriage 200B.

In all embodiments, head 142 of screw 110 may be accessed by a driving tool extending from outside the body, into the body, while endplates 102, 104 lie at an angle, for example perpendicular, to a pathway into the body. More particularly, spacers 100 of the disclosure may be inserted between vertebral bodies when in a collapsed or non-expanded state, from any approach to the spine. As spacer 100 is inserted between endplates, it is rotated to contact cortical bone of the endplates, and to avoid anatomical structures which should not be disturbed.

Once rotated into position, screw support 160 can be turned towards an exterior of the body, if it has not already been so turned, whereby a tool may be conveniently mated with a tool engagement 188 of screw head 142. After screw 110 is rotated, endplates 102, 104 separate, expanding or increasing a height of spacer 100, and restoring and maintaining a therapeutic spacing between adjacent bones. In some embodiments, after expansion of spacer 100, screw support 160 may slide along flanged connection 162 to lie at an optimal orientation with respect to body tissue, for example 0 degrees with respect to carriage 200, or at an angle deemed best by the medical practitioner.

Spacers 100 may include ramps 150, 250 of differing height within a spacer, whereby endplates 102, 104 mutually separate at different rates at distal and proximal ends 154, 156, or at sides transverse to distal and proximal ends 154, 156, whereby an angular disposition of adjacent bones may be changed, for example to correct lordosis or scoliosis. Endplates 102, 104 may additionally, or alternatively, be resilient, so that they may conform to bony surfaces, forming a more stable support platform. Accordingly, endplates 102, 104 can be fabricated from a polymeric material, a naturally resilient material, or a resilient metal, for example a shape memory alloy, or any other resilient biocompatible material of sufficient strength and durability for separating bones within the body. Spacers 100 may further be removed or repositioned during an initial implantation procedure, or later in time.

In accordance with the disclosure, during implantation of intervertebral spacers from a posterior approach, there is a need to avoid damaging nerve roots. A prior art spacer dimensioned to separate bones can block a view of nerve roots as it is inserted, and due to its large size, poses a greater risk of contacting nerve roots during insertion into the body. As a result, the medical practitioner must more often retract nerve roots, with attendant danger of tissue damage. Spacers 100 of the disclosure form a smaller dimension during implantation, relative to a final dimension for spacing bones. Accordingly, nerve roots can be visualized and avoided during insertion, and nerve root manipulation can be avoided or minimized.

As spacers 100 of the disclosure can be articulated during implantation, they can be inserted between bones by being passed through a minimally invasive entry, for example through an incision approximating the smallest collapsed dimension, for example transverse to a longitudinal dimension extending between distal and proximal ends 154, 156. This enables exceptional anterior placement without impaction, as well as facilitating implantation from other approaches. Implants of the disclosure further develop a good bone contact area, as an implant with a larger footprint may be inserted through a reduced size incision, due to the overall dimensions of the implant being reduced during insertion.

Spacers 100 of the disclosure enable a continuous expansion and retraction over a range of displacements according to predetermined dimensions of a specific spacer design. This provides the ability to distract vertebral bodies or other bones to a desired height or separation. Endplates 102, 104 can be shaped to form planes or surfaces which converge relative to each, to provide for proper lordosis, and can be provided with openings 190 through which bone may grow, and into which bone graft material may be placed. Spacers 100 of the disclosure may be used to distract, or force bones of a joint apart, or may be used to maintain a separation of bones created by other means, for example by a retractor. Endplates may additionally be curved to conform to the surface of body tissue, for example the surface of cortical bone, of the vertebra to be contacted, for improved fixation and load bearing.

Spacers 100 of the disclosure may be further secured in connection with the body by passage of elongated fasteners through frame 162, or an endplate 102, 104. As described therein, a blocking mechanism can be used to prevent backing out of the elongated fastener. Similarly, screw 110 can be provided with a blocking mechanism as described in the foregoing reference, or a resilient washer (not shown) may be positioned within groove 186, to resist unintended rotation of screw 110.

Implants of the disclosure may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material.

Portions or all of the implant may be radiopaque or radiolucent, or materials having such properties may be added or incorporated into the implant to improve imaging of the device during and after implantation.

Spacers 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of spacers 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of the implants of the disclosure. For example, polymeric portions can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example an angular mating disposition of endplates, to provide for a natural lordosis, or a corrective lordosis, for example of from 0° to 12° for a cervical application, although much different values may be advantageous for other joints. Lordotic angles may also be formed by shaping one or both endplates to have relatively non-coplanar surfaces.

Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Spacers 100 may be implanted within any level of the spine, and may also be implanted in other joints of the body, including joints of the hand, wrist, elbow, shoulder, hip, knee, ankle, or foot.

In accordance with the invention, a single spacer 100 may be used, to provide stabilization for a weakened joint or joint portion. Alternatively, a combination of two, three, or more of any of spacer 100 may be used, at a single joint level, or in multiple joints. Moreover, implants of the disclosure may be combined with other stabilizing means.

Additionally, spacers 100 of the disclosure may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

Any surface or component of an implant of the disclosure may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, spacer 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position spacer 100 may be performed through an Anterior, Anterolateral, Posterolateral, lateral or any approach.

In a typical embodiment, spacer implants of the disclosure have an uncompressed height, before insertion, of 7 to 13 mm, and may advantageously be provided in cross-sections of 10×27 mm, 12×32 mm and 12×37 mm, with 4, 8, 12, or 16 degree lordotic angles, although these are only representative sizes, and substantially smaller or larger sizes can be therapeutically beneficial. In one embodiment implants in accordance with the instant disclosure are sized to be inserted using an MIS approach, for example using a reduced incision size, for example less than about 5 cm, and advantageously less than about 2.5 cm, with fewer and shorter cuts through body tissue. Spacer 100 may advantageously be used in combination with other known or hereinafter developed forms of stabilization or fixation, including for example rods and plates.

Spacer implants of the disclosure can be inserted into the body, advantageously in a contracted or non-expanded configuration, through a transforaminal approach, and can articulate in attachment to an inserter tool (not shown), for example for anterior placement. Once placement is achieved, the implant is capable of expanding for disc height restoration. To maintain an engagement spacer 100 and an insertion tool, a driving end (not shown) of the tool is inserted into tool engagement 188. To prevent separation of the tool and spacer 100, a tool connector 192 may be provided, extending from or formed within screw support 60. In the embodiment shown in FIG. 16, for example, tool connector 192 extends from a surface of screw support 60B, and is releaseably grasped by a mating tool portion.

Portions of spacer 100 may be radiopaque or radiotransparent. To improve visibility under imaging, radiopaque elements 194 may be provided in predetermined locations within spacer 100. In the embodiment of FIG. 16, for example, elements 194 are positioned within at least one of endplate 102B, 104B.

Implant spacers 100 of the disclosure can be positioned anterioriorly and continuously expanded to provide axial balance and greater endplate contact area, and allow for superior sagittal correction, and are insertable into the body through a smaller window, decreasing the need for damage and trauma to body tissue. Spacers 100 of disclosure provide the benefits of an ALIF device, implantable through a familiar posterior approach, decreasing surgery time and associated blood loss, as well as eliminating the need for an access surgeon.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An expandable intervertebral spacer, the spacer comprising:
a frame having a first angled surface and a second angled surface;
a connector having an upper surface and a lower surface;
a first endplate having an upper surface and at least one angled surface engageable with the first angled surface of the frame;
a second endplate having a lower surface and at least one angled surface engageable with the second angled surface of the frame;
an actuating screw contacting the connector and the frame, rotation of the actuating screw results in the first endplate and the second endplate moving away from each other from a first position to a second position,
wherein the first endplate and the second endplate each include a recess, at least a portion of the connector is received in the recess of the first endplate and at least another portion of the connector is received in the recess of the second endplate,
wherein in the first position the upper surface of the connector is substantially aligned with the upper surface of the first endplate along a horizontal plane and the lower surface of the connector is substantially aligned with the lower surface of the second endplate along a second horizontal plane, and
wherein the spacer has a curved longitudinal axis when viewed from a position normal to the upper surface of the first endplate.

2. The spacer of claim 1, wherein in the second position the upper surface of the connector is not generally aligned with the upper surface of the first endplate and the lower surface of the connector is not aligned with the lower surface of the second endplate.

3. The spacer of claim 1, wherein in the second position the upper surface of the first endplate is located above the upper surface of the connector and the lower surface of the second endplate is located below is the lower surface of the connector.

4. The spacer of claim 1, wherein the connector includes a flanged portion, at least a portion of the flanged portion is received in the recess of the first endplate and at least a portion of the flanged portion is received in the recess of the second endplate.

5. The spacer of claim 4, wherein the flanged portion of the connector and the recess of the first endplate form a dovetail connection and wherein the flanged portion of the connector and the recess of the second endplate form a dovetail connection.

6. The spacer of claim 5, wherein the recess of the first endplate and the recess of the second endplate both extend generally vertically.

7. The spacer of claim 6, wherein the flanged portion of the connector that is received in the recesses of the first and second endplates slides within the recesses of the first and second endplates when the first and second endplates move from the first position to the second position.

8. The spacer of claim 1, wherein the first endplate, the second endplate and the frame each include at least one vertically extending through hole.

9. The spacer of claim 8, wherein the through holes of the first endplate, the second endplate, and the frame are at least partially aligned vertically in the first position and in the second position.

10. The spacer of claim 1, wherein the first endplate and the second endplate each have a distal portion and a proximal portion, the distal portions of the first and second endplates are at least partially arcuate.

11. The spacer of claim 1, wherein the first endplate includes a plurality of protrusions on the upper surface and the second endplate includes a plurality of protrusions on the lower endplate.

12. The spacer of claim 1, wherein rotation of the actuation screw in a first direction results in the first endplate and the second endplate moving away from each other and rotation of the actuation screw in a second direction results in the first endplate and the second endplate moving toward each other.

13. An expandable intervertebral spacer, the spacer comprising:
- a frame having a first angled surface sloping in a first direction and a second angled surface sloping in a second direction;
- a connector having an upper surface and a lower surface and a flanged portion;
- a first endplate having an upper surface and at least one angled surface engageable with the first angled surface of the frame;
- a second endplate having a lower surface and at least one angled surface engageable with the second angled surface of the frame;
- an actuating screw contacting the connector and the frame, rotation of the actuating screw in a first direction results in the first endplate and the second endplate moving away from each other from a first position to a second position,
- wherein the first endplate and the second endplate each include a recess, at least a portion of the flanged portion of the connector is received in the recess of the first endplate and at least another portion of the flanged portion of the connector is received in the recess of the second endplate,
- wherein the flanged portion of the connector and the recess from the first endplate form a dovetail connection,
- wherein the flanged portion of the connector and the recess from the second endplate form a dovetail connection,
- wherein the frame includes a vertically extending through hole, the through hole being bounded on each side by a portion of the frame,
- wherein a first end of the upper surface of the first endplate, a second end of the lower surface of the second endplate, and lateral sides of the first and second end plates taper towards a distal end of the spacer, and
- wherein the spacer has a curved longitudinal axis when viewed from a position normal to the upper surface of the first endplate.

14. The spacer of claim 13, wherein in the first position the upper surface of the connector is generally aligned with the upper surface of the first endplate and the lower surface of the connector is generally aligned with the lower surface of the second endplate.

15. The spacer of claim 14, wherein in the second position the upper surface of the first endplate is located above the upper surface of the connector and the lower surface of the second endplate is located below is the lower surface of the connector.

16. The spacer of claim 13, wherein the recess of the first endplate and the recess of the second endplate both extend generally vertically.

17. The spacer of claim 16, wherein the flanged portion of the connector that is received in the recesses of the first and second endplates slides within the recesses of the first and second endplates when the first and second endplates move from the first position to the second position.

18. The spacer of claim 13, wherein the first endplate and the second endplate each include at least one vertically extending through hole.

* * * * *